(12) United States Patent
Pierson et al.

(10) Patent No.: US 8,602,260 B2
(45) Date of Patent: Dec. 10, 2013

(54) IMPRESSION MATERIAL DELIVERY SYSTEM

(75) Inventors: Paul Richard Pierson, Camden, DE (US); Tony Bonanno, Felton, DE (US); Robert Pieroni, Milford, DE (US)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 13/450,534

(22) Filed: Apr. 19, 2012

(65) Prior Publication Data

US 2012/0267394 A1 Oct. 25, 2012

Related U.S. Application Data

(60) Provisional application No. 61/476,968, filed on Apr. 19, 2011.

(51) Int. Cl.
*B65D 35/22* (2006.01)
(52) U.S. Cl.
USPC .............................................. 222/94; 222/102
(58) Field of Classification Search
USPC ........... 222/94, 92, 97–102, 214, 145, 5, 210, 222/206, 202, 216, 145.5, 162, 391, 222/325–327; 383/80
See application file for complete search history.

(56) References Cited

U.S. PATENT DOCUMENTS

| | | | | |
|---|---|---|---|---|
| 2,064,357 | A * | 12/1936 | Ritterbusch | 222/93 |
| 2,550,537 | A * | 4/1951 | Derrick | 222/102 |
| 3,187,951 | A * | 6/1965 | Hardman et al. | 222/102 |
| 3,302,832 | A | 2/1967 | Hardman et al. | |
| 3,860,147 | A * | 1/1975 | Vessio et al. | 222/96 |
| 3,946,904 | A * | 3/1976 | Mulakala | 222/102 |
| 5,318,203 | A | 6/1994 | Iaia et al. | |
| 5,386,928 | A * | 2/1995 | Blette | 222/94 |
| 5,697,524 | A | 12/1997 | Sedlmeier | |
| 5,897,028 | A | 4/1999 | Sauer | |
| 6,364,165 | B2 * | 4/2002 | Sampson et al. | 222/102 |
| 6,752,264 | B2 | 6/2004 | Versluys | |
| 6,845,884 | B2 | 1/2005 | Chan et al. | |
| 6,854,621 | B2 | 2/2005 | Keller | |
| 7,731,413 | B2 | 6/2010 | Busin et al. | |
| 7,841,481 | B2 * | 11/2010 | Gleich | 220/23.4 |

\* cited by examiner

*Primary Examiner* — Lien Ngo
(74) *Attorney, Agent, or Firm* — Leana Levin; Douglas J. Hura; David A. Zdurne

(57) ABSTRACT

Disclosed herein is a device suitable for the delivery of dental materials, such as impression material. The device disclosed herein includes a cartridge that has at least two separate pouches and a spout.

7 Claims, 19 Drawing Sheets

IMPRESSION MATERIAL DELIVERY SYSTEM

This application claims priority to U.S. Provisional Patent Application No. 61/476,968, filed on Apr. 19, 2011.

FIELD OF THE DISCLOSURE

Disclosed herein is a device intended for the packaging and delivery of dental impression materials. Specifically, the disclosed device is practical for two-component, paste-like products, but could easily be adapted to single component materials. In addition, this device could be useful for other dental products such as pastes, composites, cements, adhesives and other formulated products. The product applications for the disclosed device also extend beyond dentistry and could find useful application in industrial or commercial adhesives, epoxies or medicaments.

BACKGROUND

Present devices known in the art are rigid, plastic cartridges that are typically used for impression materials (i.e. the Mixpac® 50 mL cartridge manufactured by Sulzer Mixpac). These rigid, plastic cartridges are then removable attached to a dynamic or stationary mixing tip. The new cartridge reduces packaging waste by using flexible films and product waste by utilizing a dynamic mixtip. Another intended result is to provide the user with powered dispensing that is more ergonomic than the current manual cartridge dispensers and more portable than current dynamic mixing machines.

U.S. Pat. No. 5,318,203 describes a dual tube assembly comprised two individual tubes that are joined together by D-shaped members at the dispensing end. The ends of the tubes are joined by crimping them together. Claim one requires a hinged cap which we will not have. Also the tubes of U.S. Pat. No. 5,318,203 are hollow, semi-rigid and molded as one contiguous piece by injection molding whereas our pouch is comprised of a film laminate with an attached rigid fitment. The D-shaped members are joined together by snaping on the hinged cap which engages with an annular snap ring on the outer rounded surface of each D-shaped member.

U.S. Pat. No. 6,752,264 describes a spout pack with a double pouch configuration. The pouches of U.S. Pat. No. 6,752,264 are side by side with the fin seal separating the two pouches as opposed to our configuration which has two separate pouches positioned one on top of the other. This patent also has a single fitment that has two ports with a passageway to each compartment.

U.S. Pat. No. 3,302,832 illustrates a powered dispenser which delivers material from two independently mounted tubes. The tubes roll up on gear mounted rollers to express the material.

U.S. Pat. No. 7,731,413 describes a dynamic mixtip that incorporates a static mixing element into the outer housing of the mixtip.

EP0800994 discloses a manufacturing method for making spout packs and heat sealing the spout fitment onto flexible films.

U.S. Pat. No. 5,697,524 describes the so called sausage packs attached to a rigid base. The packs are closed until acted upon by pressure which causes them to contact piercing elements that puncture them and releases the material through an outlet.

U.S. Pat. No. 5,897,028 discloses a hand held dispenser for sausage packs which has piercing members in the front to open the packs and plungers to compress the packs.

U.S. Pat. No. 6,845,884 describes a tooth paste tube that has a tube-within-a-tube construction. The inner tube is said to be substantially rigid material and non-displaceable in response to compressive force.

U.S. Pat. No. 6,854,621 describes a typical dynamic mixer for dispensing bulk impression materials. The device requires a drive shaft positioned between the barrels of a double cartridge and the mixer to have a locating means for positioning the cartridges with various ratios.

SUMMARY

The cartridge device disclosed herein reduces packaging waste by using flexible films, and also reduces product waste by utilizing a dynamic mixtip. Another intended result is to provide the user with a powered dispensing unit that is more ergonomic than conventional manual cartridge dispensers and more portable than current dynamic mixing machines.

DETAILED DESCRIPTION

Figure 2:
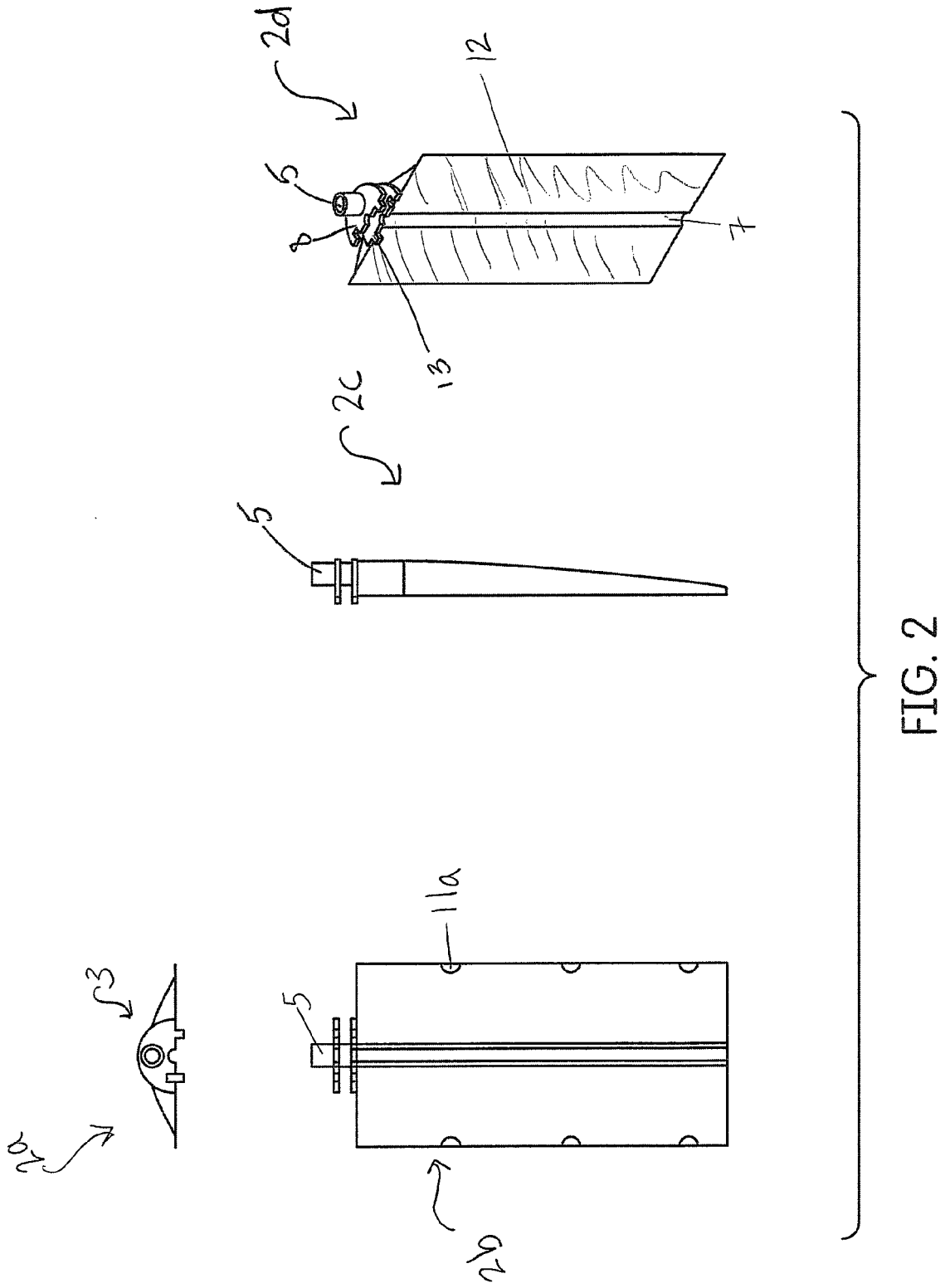
FIG. 2 demonstrates rollers that are capable of squeezing material out of the cartridge described herein.
Figure 14:
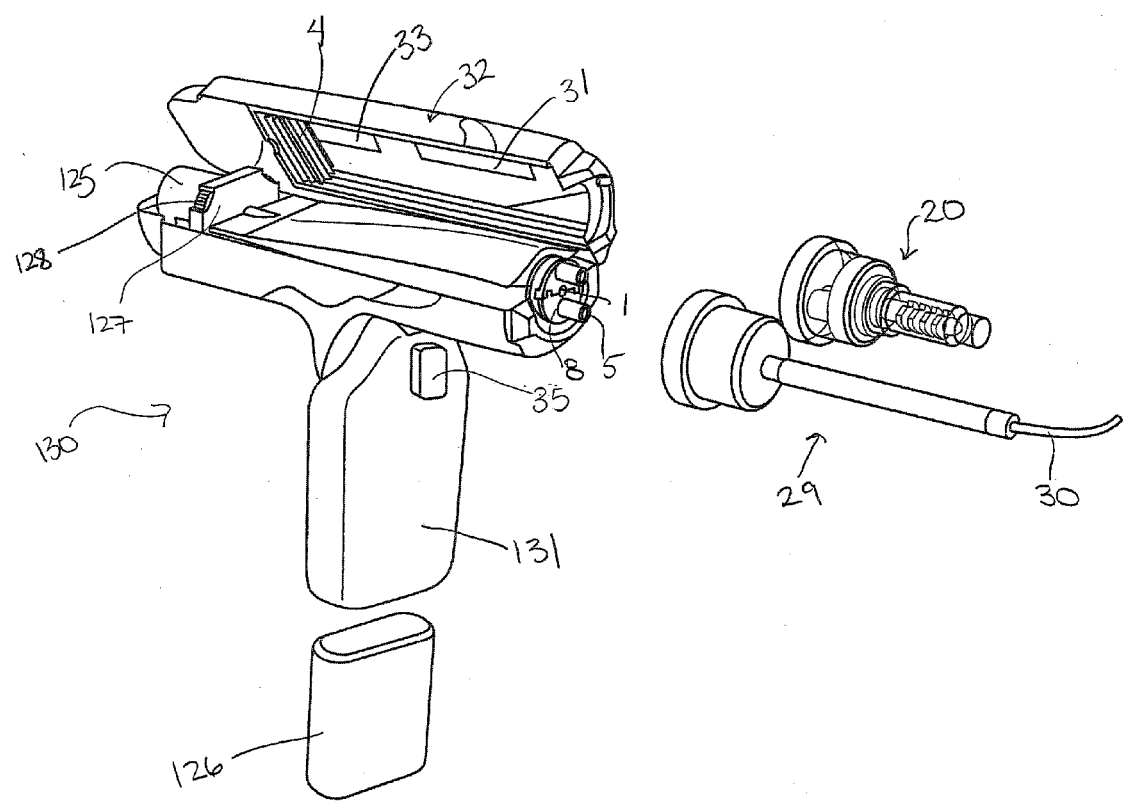
FIG. 14 shows a handpiece configured in a shape of a gun.
Figure 15:
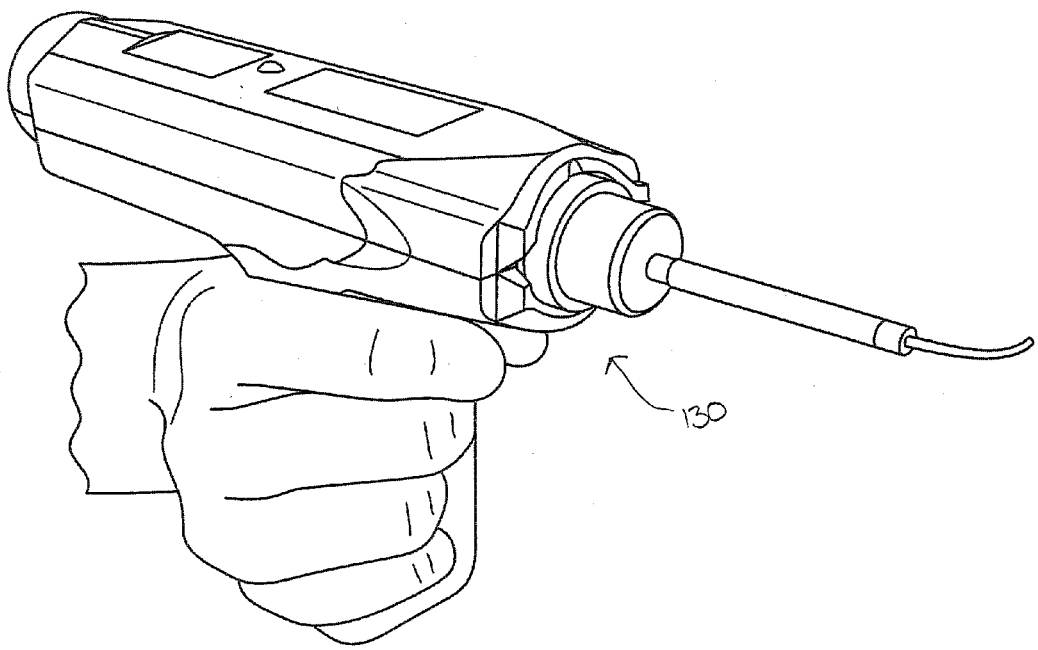
FIG. 15 illustrates the gun-shaped handpiece in a user's hand.

Disclosed herein is a device suitable for the delivery of impression material, that is, a device capable of extruding at least two dental materials. The device disclosed herein includes a cartridge 100 that has at least two separate pouches (a single pouch is represented in FIG. 2) and a spout 5. The at least two separate pouches are attached to the spout through a connector portion 9. The connector portion includes a D-shaped connector 8 for each of the two pouches such that heat seal fins 6 suitable for sealing each D-shaped connector 8 to form the connector portion are present and a notch 7 in the heat seal fins 6 is present for the drive shaft 1. The cartridge 100 is placed inside an assembly that assists in extruding the dental material from the pouches. For example, the assembly may include rollers 4 that are capable of assisting in the extrusion of the dental material. The device contains the cartridge and may be of any suitable shape such that it extrudes the dental material of the at least two pouches of the cartridge, for example an elongated delivery device, such as a pen shaped device (FIGS. 10 and 13) or a gun-shaped device (FIGS. 14 and 15).

Although the dispensing device described herein is described as having a cartridge of two pouches, a person of ordinary skill in the art will understand that the cartridge herein may have more than two pouches, depending upon the number of materials to be combined and extruded from the delivery device. If more than two pouches are present, then such pouches would be connected to each other by any suitable method. In other words, the connector may have a shape other than the D-shaped connector 8 described herein and depicted in the Figures. Moreover, the dispensing device described herein and demonstrated in the Figures depicts a specific shape and design for the pouches of the cartridge. However, one of ordinary skill in the art will understand that the pouches may be of different shape and encased in a pouch container in order to form a suitable cartridge.

Figure 1:
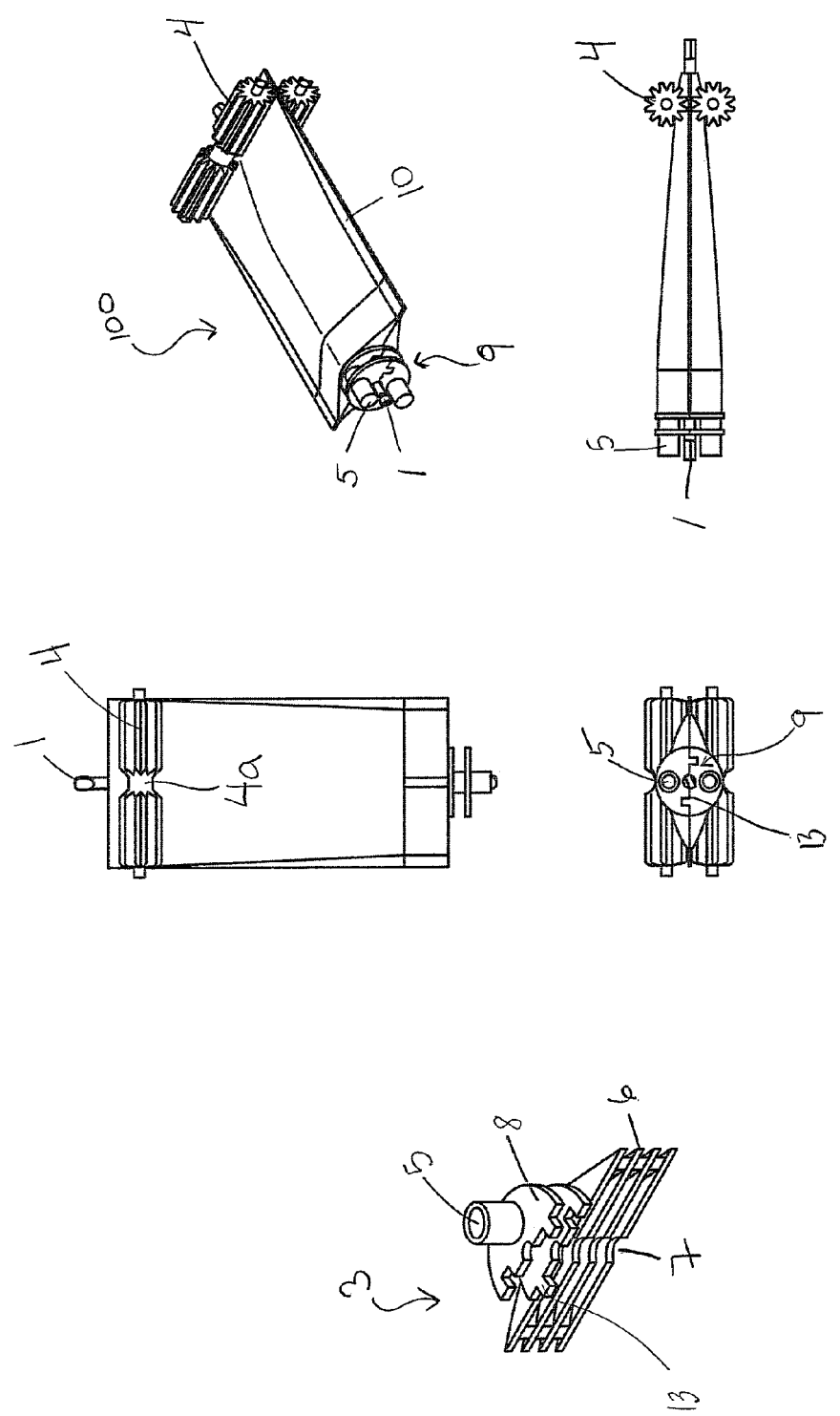
FIG. 1 demonstrates a cartridge of one embodiment having a spout fitment and drive shaft.

FIG. 1 documents the initial mechanical drawing of the cartridge showing a connector portion 9 and drive shaft 1. It also records the concept of making two separate pouches (for example, one pouch for a base and one pouch for a catalyst) and joining them together to make a complete cartridge assembly 100. In an embodiment, one half of the connector portion 9 may be considered a D-shaped connector 8 with interlocking members 13 that snap or fit together to form a dual component cartridge 100. As explained herein, the connector may have a shape other than the D-shaped connect 8 depicted in the Figures when more than two pouches are used or when the cartridge is of a different configuration.

FIG. 2 illustrates the assembly of a flexible film cartridge 100 of FIG. 1, hereafter also referred to as the cartridge. Individual pouches as demonstrated in FIG. 2 like these are commonly referred to as spout packs because they have rigid plastic spout fitments (also referred to as a connector portion) 9. The body of the pouch 2d is comprised of a multi-layer film laminate: The laminate has an inner heat seal layer 12 which is used for forming the end and side seals of the pouch 2. The heat seal layer 12 also adheres to lower the ribs 6 of the connector portion 3 to complete a formed spout pack or cartridge 100.

In this embodiment, the connector portion 3 has a groove 7 for the drive shaft 1 to pass through. When the film laminate 12 is sealed to the connector portion 3 the film is pressed into the groove to form a channel 7 for the drive shaft 1.

A connector portion 3, as demonstrated in FIG. 2, has triangular sealing ribs 6 having one long side and two shorter opposite sides. This configuration permits two pouches to be joined together along the long sides forming the cartridge assembly 100.

The connector portion may be a rigid material, such as plastic, polymer, metal or the like, that contains a lower portion of heat sealing members, usually having from about one to about five ribs that may heat seal to the inner layer of the flexible film laminate 12. The upper portion of the connector portion 3 may be a D-shaped connector section 8 that facilitates the joining of two pouches together by snap members, interlocking portions or the like 13. Keyed elements such as tabs and mating pockets permit the connector portion 3 to mate with an identical connector portion when it is turned 180°. In embodiments, the connector portions 3 snap together via the interlocking members 13 and cannot unintentionally come apart by virtue of one way snap members or sealing mechanisms which join the two pouches together.

When the D-shaped connectors 8 are joined together they may form a flange that facilitates connection with the mixtips described herein. A bayonet connection, a threaded connection, or the like may be suitable for connecting the mixtip to the flexible film cartridge.

The pouches may be a film laminate that is a monolithic film substrate or a multi-layer film laminate having an inner heat seal layer and an outer barrier layer, these layers may be a foil and/or various plastic laminations constructed for specific barrier properties necessary to increase the shelf life, increase pouch durability, reduce film memory, or the like.

FIG. 2 shows a series of notches 11 in one side of the film laminate 2b. When the pouch is formed they fall within the boundary of the heat seal area and expose the heat seal layer on the opposite side of the pouch. When two pouches are joined together the heat seal areas of the two pouches can be heat sealed together, thereby forming the cartridge assembly 100.

The pouches can be made and filled by forming the flexible film around the fitment and seal the fitment ribs to the inner heat sealing layer of the film laminate. Typically, the fully formed connector portion 9 may be capped prior to heat sealing so that the filling can occur in-line, as soon as the pouch is formed.

In alternative embodiments, the connector portion 3 on each pouch may be capped, plugged, or the like, prior to pouch formation or filling. As such, each pouch will have its own cap. However, it would be beneficial to the user to remove only one cap at the time of use. It is therefore envisioned, that the caps of the individual pouches are joined together when the D-shaped connectors are joined together. The caps could snap or heat seal together so that they could be removed as one piece, which is more convenient for the user.

Figure 3:
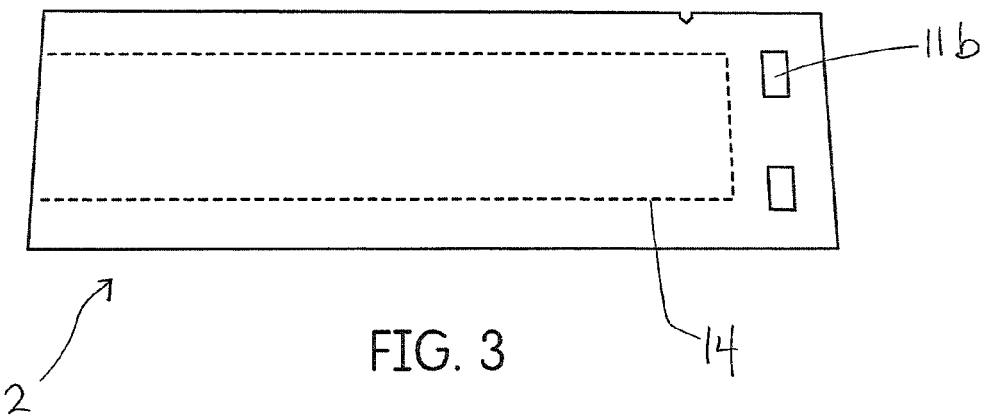
FIG. 3 illustrates the individual components of a cartridge according to embodiment described herein.

FIG. 3 illustrates the individual components of a second embodiment. The sealing ribs 6 of the connector portion 3 may be trapezoidal shaped, which is the traditional shape for spout packs. Such a configuration allows for a narrower pouch 2 having less deformation when filled. In addition, the shape of the pouch is better controlled as it collapses through the rollers. The connectors for this embodiment may be D-shaped 8 as in other embodiments.

The heat seal perimeter 14 is shown by the dashed lines. The heat sealable notches 11a shown in FIG. 2 have been replaced with two cut outs 11b near the bottom of the pouch. The cut outs 11b permit the two pouches to be sealed together at the bottom and simultaneously capture the drive shaft between the two seals for lateral alignment.

Figure 4:
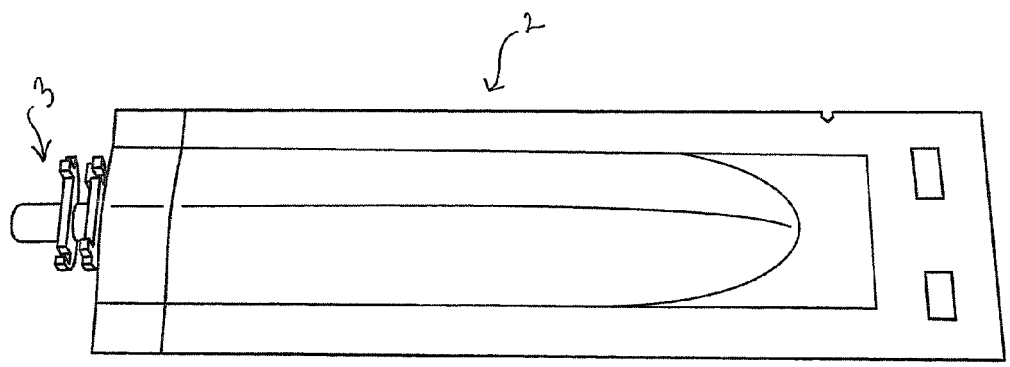
FIG. 4 illustrates one pouch of a cartridge described herein, the pouch having a spout fitment heat sealed to the pouch body.

FIG. 4 illustrates a pouch 2 with a connector portion 3 heat sealed to the pouch body. During filling, the spout fitment would be capped (not shown) to prevent the material from spilling out.

Conventionally, dynamic mixtips tend to be used with table top or bulk dispensers. However, the delivery device disclosed herein includes a dynamic mixtip attached to a hand held delivery device. Such a dispensing device incorporates the desirable benefits of a dynamic mixtip with the convenience of a handheld portable device.

The dispensing device disclosed herein is capable of utilizing dynamic mixers or static (motionless) mixers. The dynamic mixtips may be used for heavy body tray materials to reduce waste and increase dispensing rates. Static mixtips may be used for light body wash materials because they are longer than dynamic mixtips and the extra length is beneficial for intra-oral applications. The exit ports on wash materials may be configured differently than on tray materials to ensure that that the correct mixtip is always used.

One embodiment of the flexible film cartridge includes a drive shaft that is captured between the spout fitments and heat seal areas of the flexible film cartridge assembly. The drive shaft would engage a motor at the operator end of the device and the dynamic mixtip at the delivery end. The drive shaft would turn the dynamic element inside the mixtip and mix the material as it dispenses. In one embodiment, the drive shaft is eliminated from the flexible film cartridge and incorporated into the handpiece as described below.

The dynamic mixer is comprised of several injection molded plastic components. Several of these components comprise the outer housing, which supports the inner mixer and facilitates connection to the spout fitments on the flexible film cartridge.

The mixer (or mixing element) is the portion that rotates inside the housing and mixes two streams into one uniform paste.

Figure 11:
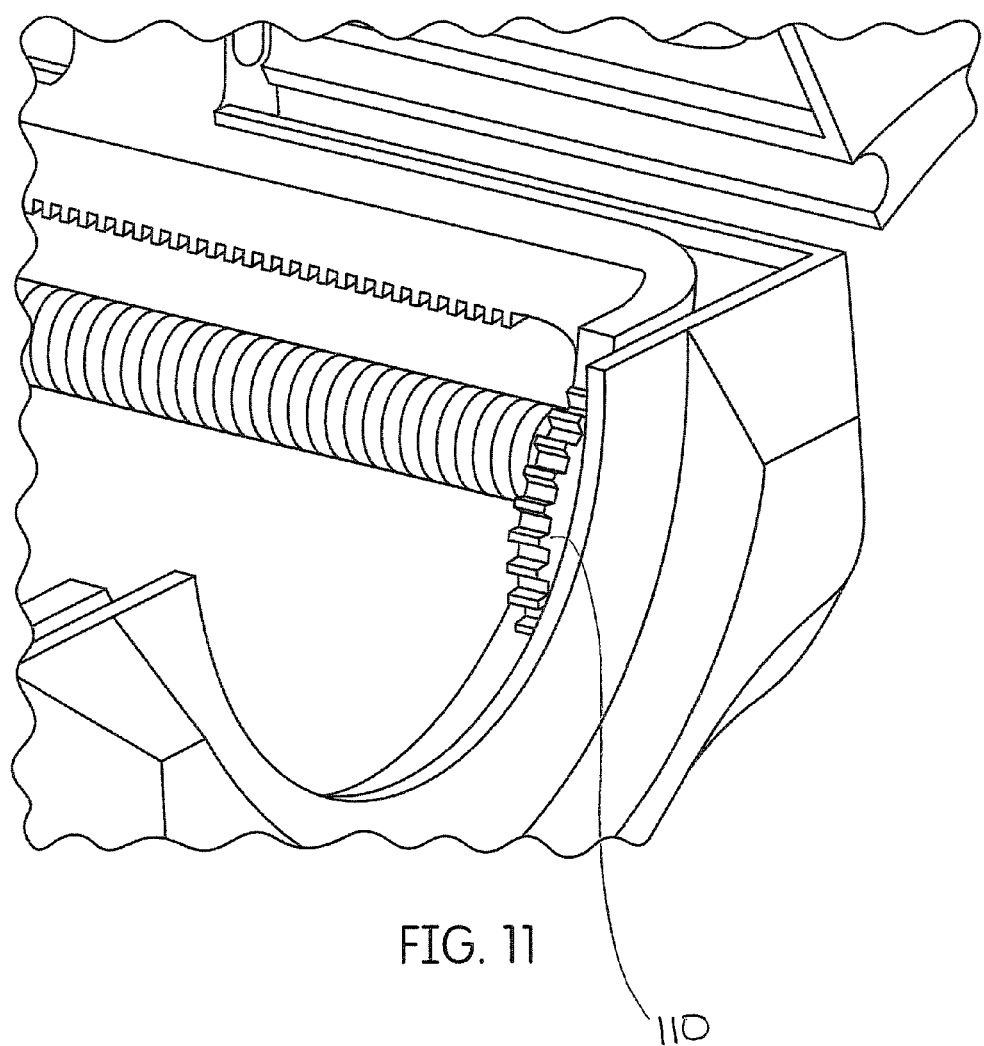
FIG. 11 illustrates a forward drive gear which will engage with a gear on the dynamic mixtip.
Figure 20:
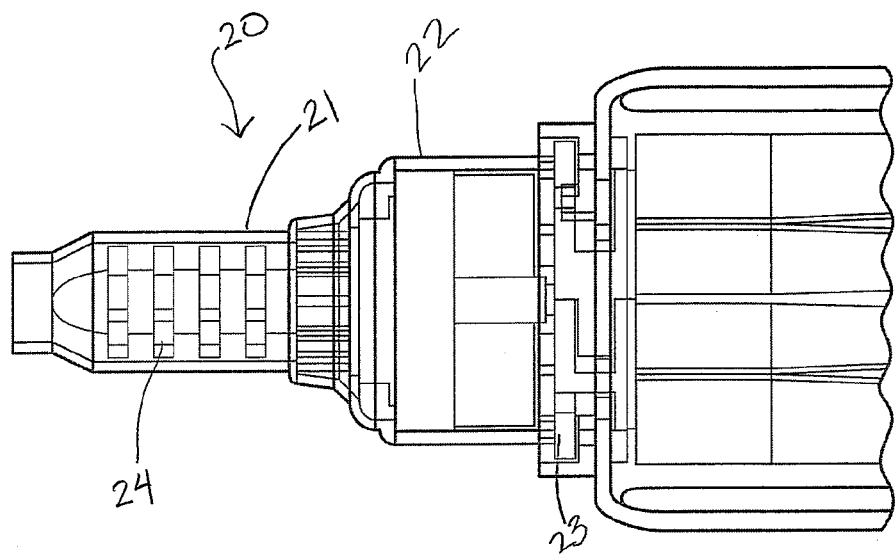
FIG. 20 is a top view of the dynamic mixtip.

FIG. 20 is a top view of the dynamic mixtip 20. The mixtip 20 and mixtip housings 21 are shown as clear material to expose the inside construction. The dynamic mixer has an elongated skirt 22 with a bayonet fitting 23 used to secure the mixtip 20 to the cartridge outlets. The dynamic element 24 is shown and rotates through a mechanical connection to either a drive shaft that extends between the pouches or between the forward gear assembly 110 as shown in FIG. 11.

Figure 16:
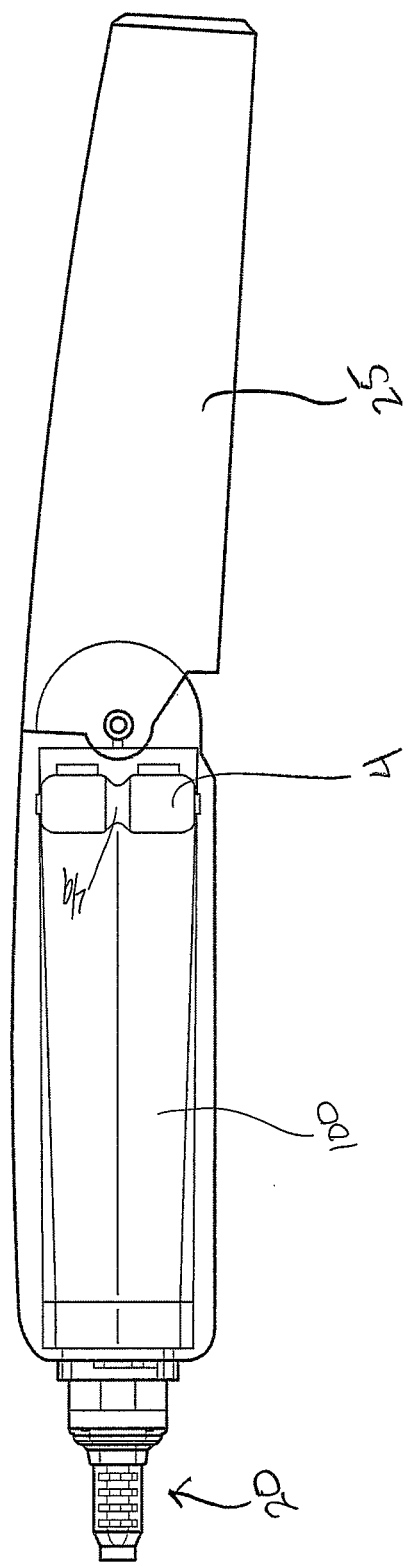
FIG. 16 illustrates an elongated handpiece having an articulated handle.
Figure 21:
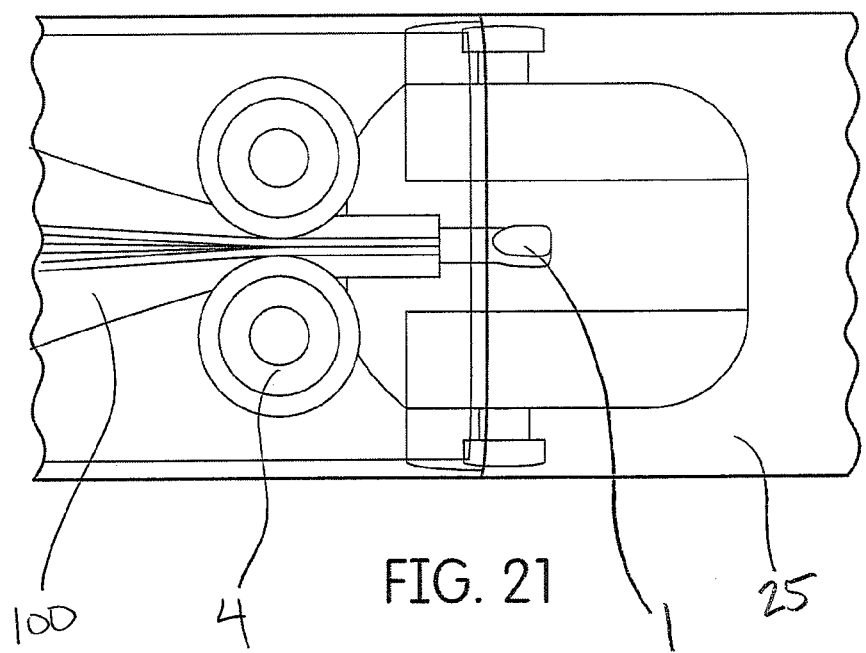
FIG. 21 shows a top view of the device shown in FIG. 16.

FIG. 21 shows a top view of the dispenser shown in FIG. 16. This view illustrates the center-style drive shaft 1 extending into the articulated handle 25 with a cartridge 100 and roller 4 assembly in position. The universal linkage and motor are not shown in this view.

Figure 22:
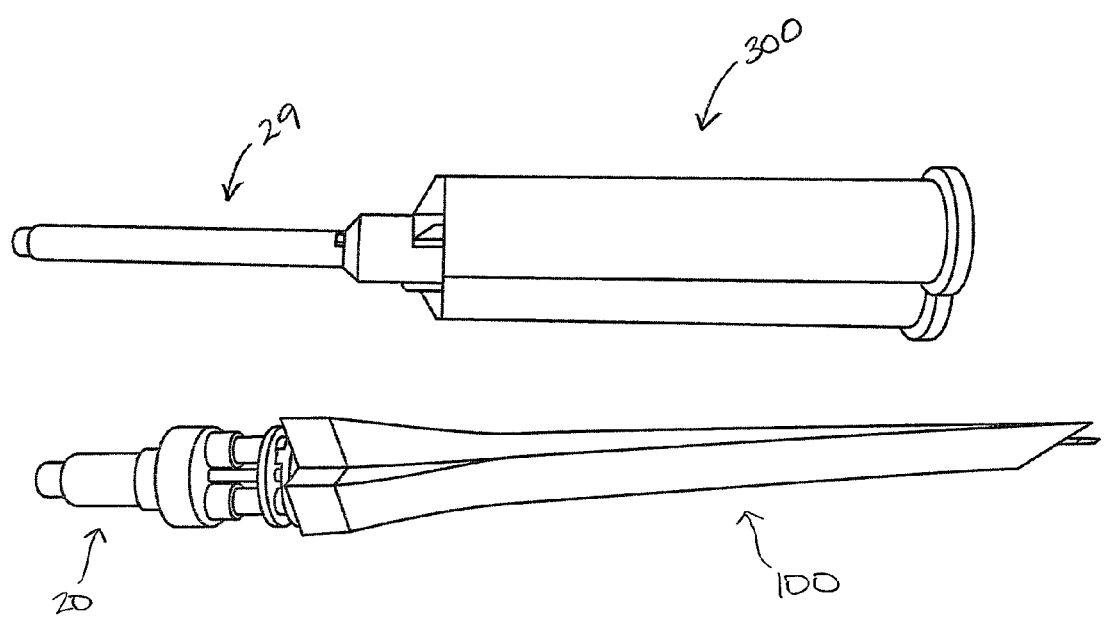
FIG. 22 shows the cartridge described herein in comparison to a conventional cartridge known in the art.

FIG. 22 shows the new cartridge 100 (bottom) in comparison to the current, conventional Mixpac cartridge (top). The dynamic mixtip 20 shown on the flexible cartridge does not have the elongated skirt as described in other embodiments.

The cartridge 100 disclosed herein may be used in conjunction with a dispensing device. The dispensing device includes an assembly that expresses or extrudes the dental materials from the pouches of the cartridge. For example, rollers 4 may be used to express material out of the cartridge 100. In one embodiment as demonstrated in FIG. 7, the assembly may include a rack 27 and pinion 28 driven by a set of worm screws 26. In another embodiment, the assembly may include a nut and screw.

FIG. 2 also shows the rollers 4 that would squeeze out the paste. Such rollers could be smooth or configured as gear teeth as shown here. Notches 4a in the rollers would permit them to roll over the cartridge without impacting the drive shaft rotation.

Figure 5:
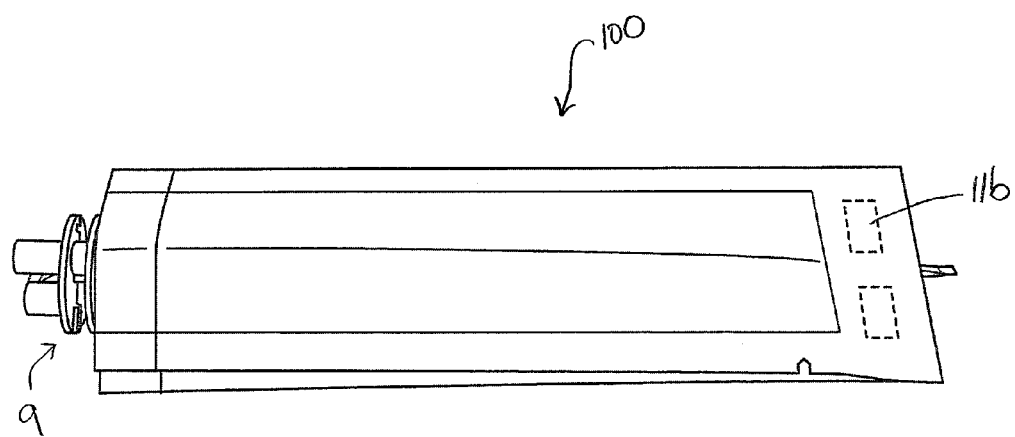
FIG. 5 shows a completed cartridge having two pouches.

FIG. 5 shows the completed cartridge 100. The connector portion are connected together and the ends are sealed 116 in the area indicated by dashed lines. The drive shaft 1 is captured between the heat sealed ends and the connector portion during assembly.

Figure 6:
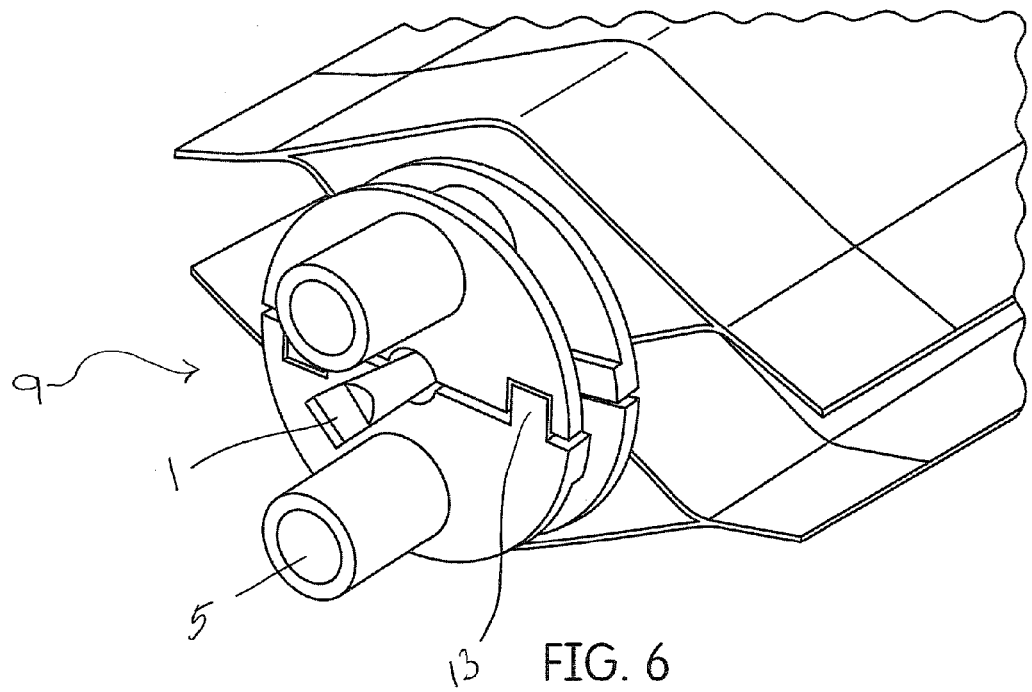
FIG. 6 illustrates a front view of an assembled cartridge.

FIG. 6 illustrates a front view of the assembled cartridge 100. The drive shaft 1 can be seen protruding through the two opposing connector portions. The interlocking members or keyed snap element 13 has been outlined in this view solely for visibility and clarity. In use the interlocking members 13 will be flush against the opposing interlocking members and not as readily apparent as in FIG. 6.

Figure 7:
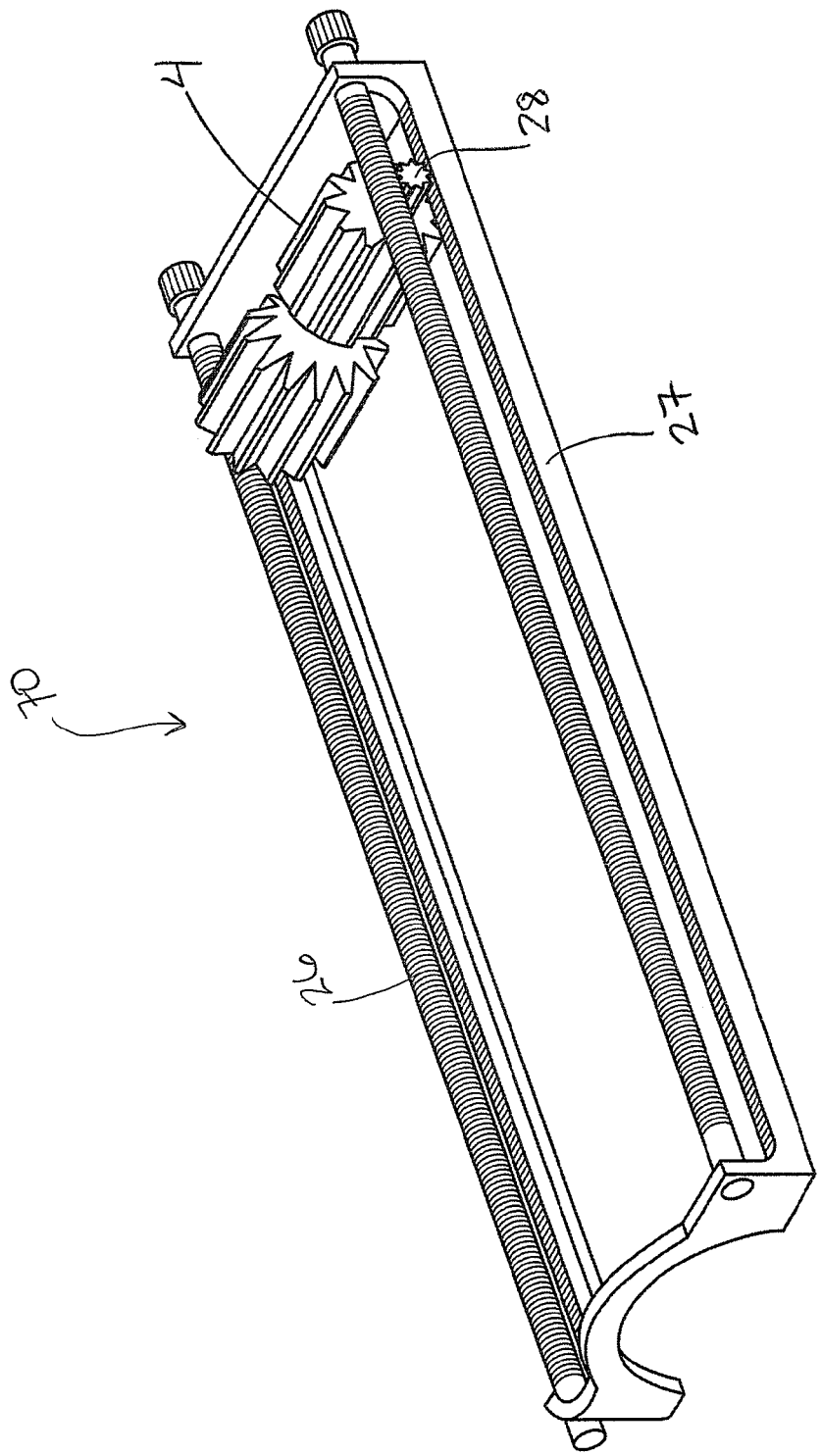
FIG. 7 illustrates a roller rack that can be used to advance the rollers in a powered dispensing device to eject the materials in the cartridge.

FIG. 7 illustrates a roller rack assembly that can be used to advance the rollers 4 in a powered dispensing device. The roller rack assembly 70 consists of a roller 4 that advances down a rack 27 and pinion 28 gear track. The pinions 28 are turned by a set of rotating worm gears 26. The worm gears 26 are turned by a transmission (not shown) which simultaneously turns the central drive shaft (not shown).

Figure 8:
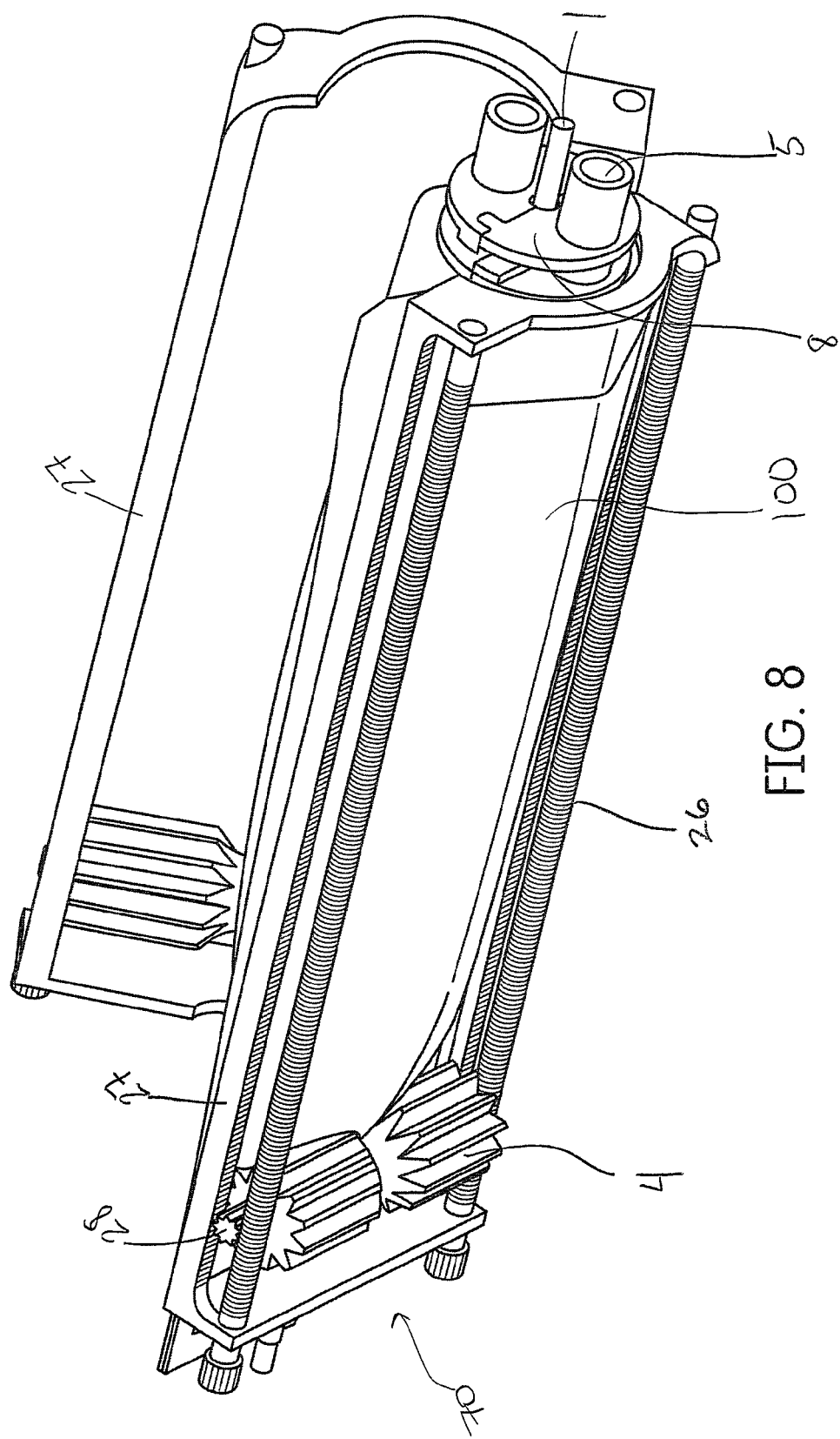
FIG. 8 shows the completed roller rack assembly in an open position.

FIG. 8 shows the completed roller rack assembly 70 having a cartridge therein 100, which consists of two hinged racks 27 that open for loading the cartridge.

Figure 9:
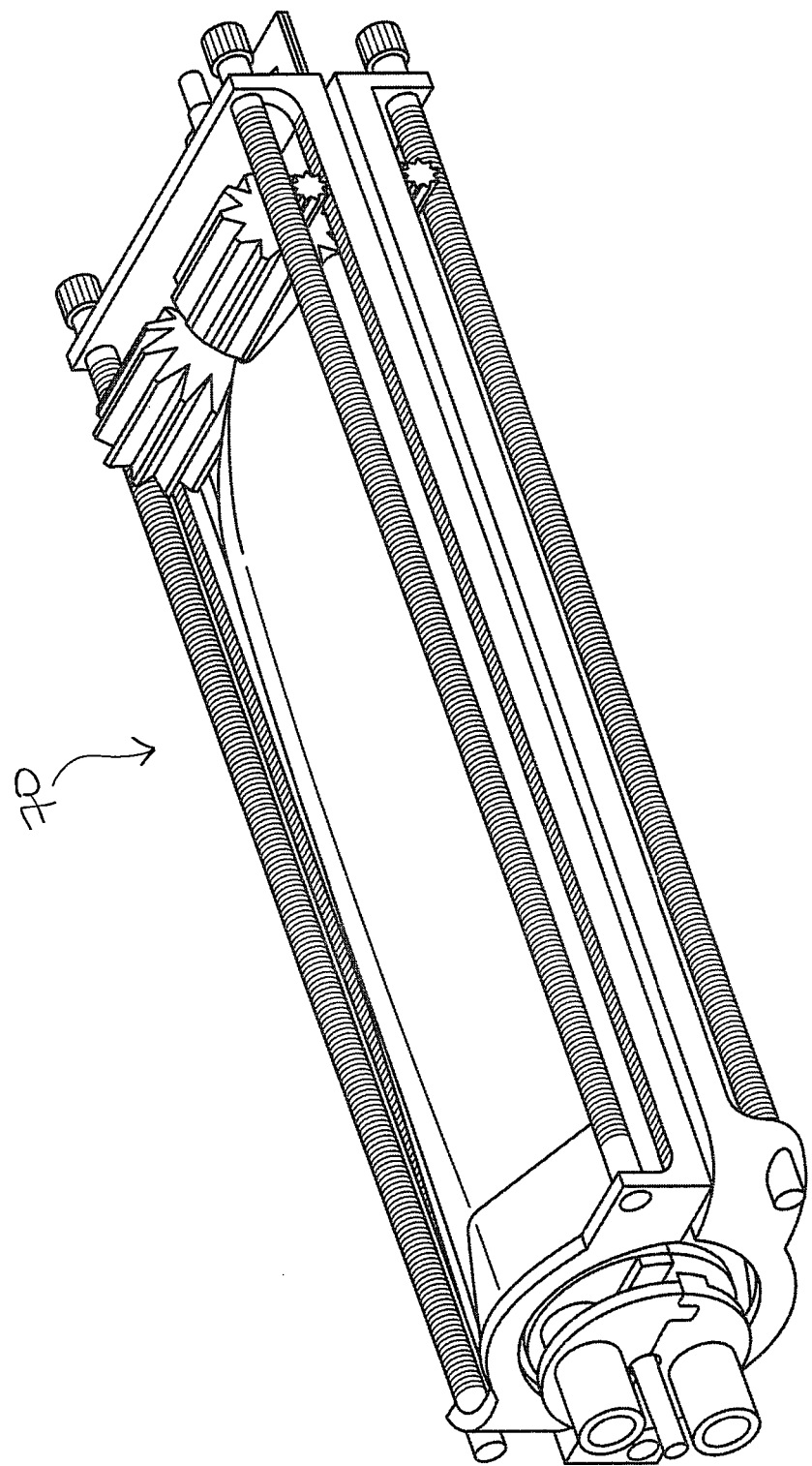
FIG. 9 illustrates the completed roller rack assembly in the closed position.

FIG. 9 illustrates the completed roller rack assembly 70 in the closed position.

The outer case of the delivery device may have an ergonomically shaped grip for the user. The outer case encloses the inner components of the delivery device and supports the flexible film cartridge 100 during use. The outer case may further include an access door for loading the cartridge, and a transparent portion or window for viewing the cartridge.

Figure 10:
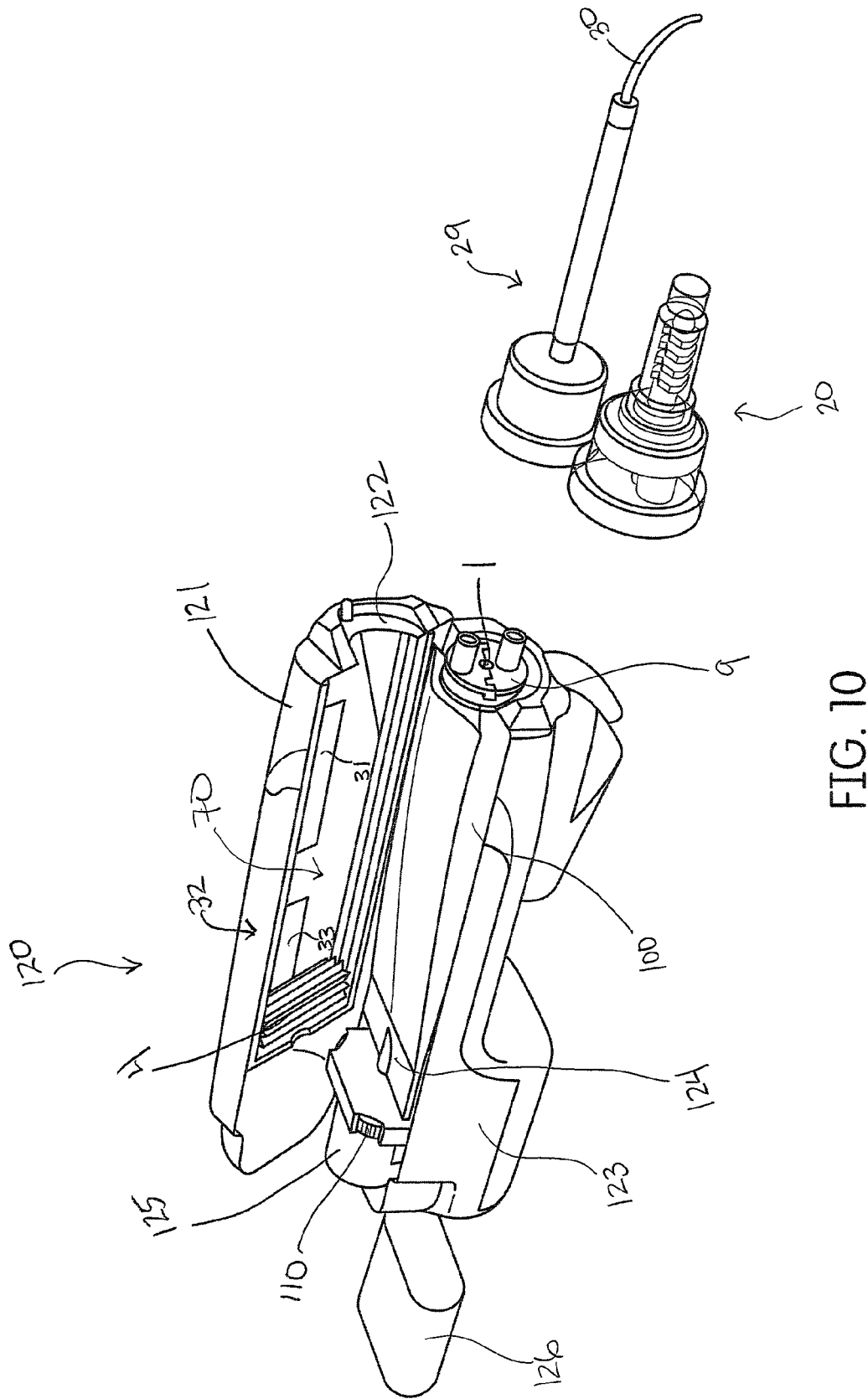
FIG. 10 illustrates an elongated handpiece.

FIG. 10 illustrates an elongated handpiece, which may be referred to as a pen-shaped dispenser. A hinged door 121 opens for cartridge 100 loading. The cartridge connector portion 9 rest in an opening 122 in the front portion of the handpiece and protrude out the front so that mixtips can be attached. Shown in FIG. 10 are a dynamic mixtip 20 and a static mixtip 29, each of which are suitable for use with the handpiece described herein. When the door is closed, the cartridge is enclosed within the roller assembly. The rollers 4 would be pre-positioned towards the rear section 123 of the roller rack prior to cartridge loading and unloading so that the rollers could properly engage with the end portion of the cartridge 124.

A gear transmission 127 may translate the motor rotation to the roller assembly 70 and shaft 1, which drives the dynamic mixtip 20. If a static mixtip 29 is utilized, then a shaft does not engage or drive the static mixtip 29. A motor may provide the mechanical motion necessary to advance the working mechanisms in the delivery device. A lithium ion battery, or any alternative suitable battery, may provide portable power for the device. Such a battery may be installed permanently or it could be removable. The delivery device may further include a printed circuit board for mounting electronic components.

A gear transmission 127 and motor 125 can be seen immediately behind the pouch. A battery pack 126 is shown in exploded view behind the handpiece and will fit into a space underneath the motor 125 and gear transmission 127.

Two mixtips are shown in this exploded view. A dynamic mixtip 20 appears in the foreground, which will be used for heavy body tray materials. The longer, narrower mixtip is a static mixtip 29 for light body wash materials and is shown with a curved intra-oral tip for dispensing material around a tooth. The static mixtip 29 also allows better intra-oral access when using wash materials FIG. 11 illustrates the forward drive gear 110 which will engage with a gear on the dynamic mixtip (not shown). The cartridge has been removed for clarity in this view.

Figure 12:
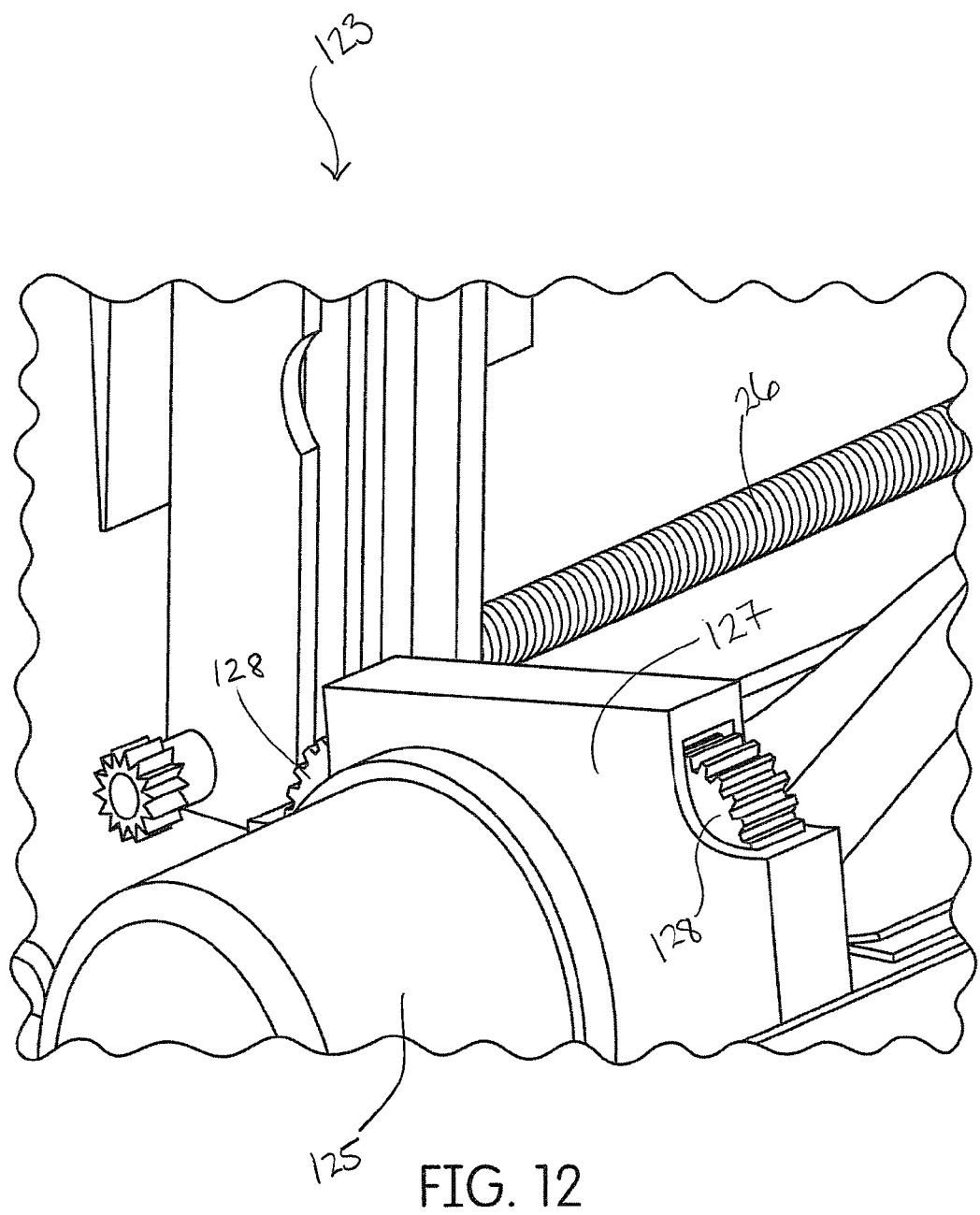
FIG. 12 illustrates a rear view of the handpiece with the door open showing the motor and transmission box. The transmission box gears engage the worm gears when the door is closed.

FIG. 12 illustrates a rear view of the handpiece 123 with the door open showing the motor 125 and transmission box 127. The transmission box gears 128 engage the worm gears 26 when the door is closed.

Figure 13:
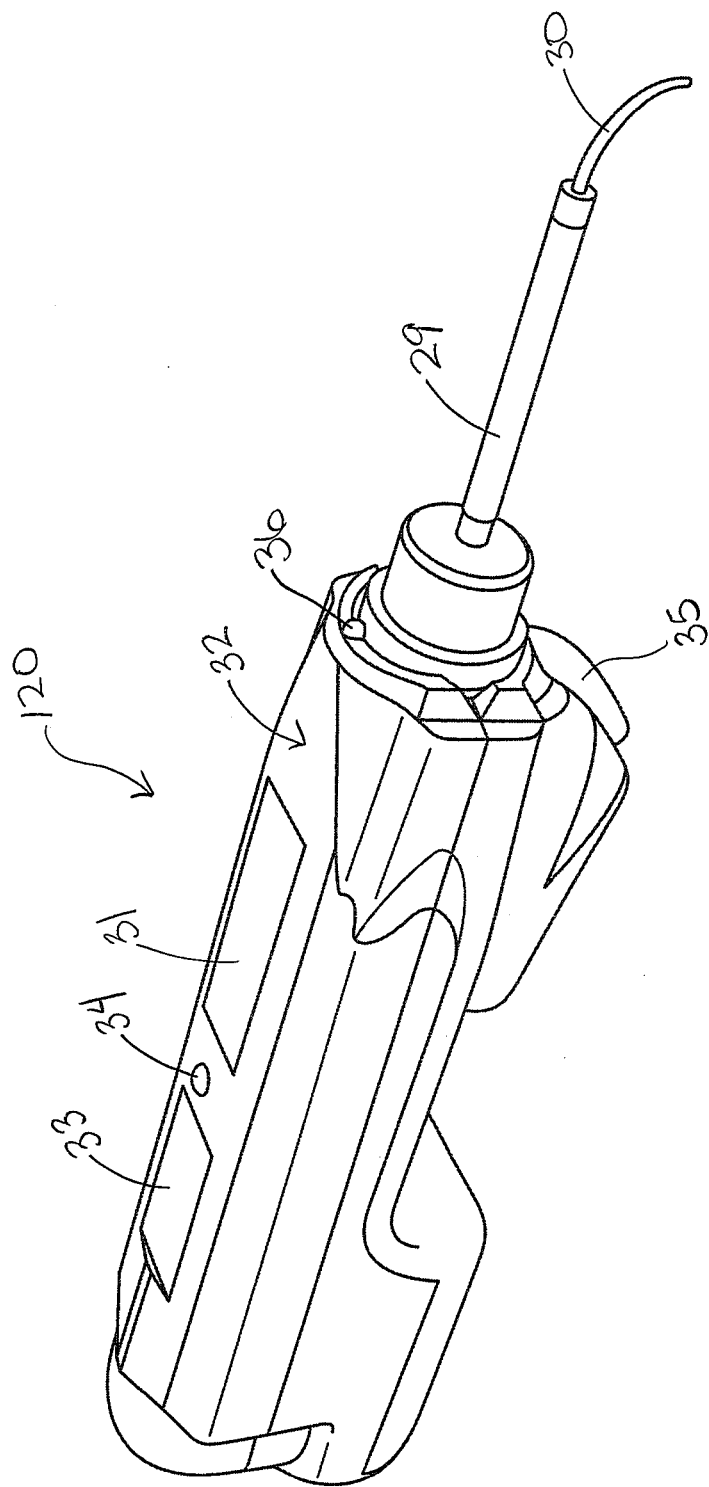
FIG. 13 shows the elongated handpiece in the ready to use state with a static mixtip and curved intra-oral tip.

FIG. 13 shows the pen-shaped dispenser 120 in the ready to use state with a static mixtip 29 and curved intra-oral tip 30. The door 32 has a clear window 31 so that the user can see what material is inside. The outer case door also includes a button 34 for changing the program settings, a digital display window 33 for data communication such as battery life and amount left in the cartridge. The dispenser also has a trigger 35 located at the front of the handpiece and an illumination light 36, such as a light emitting diode, on the front to illuminate the oral cavity.

The handpiece shown in FIG. 14 has similar mechanical functions, but is configured to be gun-shaped handpiece. In this embodiment, the battery pack 126 is relocated to the handle 131. The handle 131 may be positioned forward which balances the weight over the hand for a more balanced ergonomic effect. This configuration permits the user to get closer to the application site for greater control and precision.

FIG. 15 illustrates the gun-shaped dispensing unit 130 in an operators hand for perspective.

FIG. 16 illustrates another concept with an articulated handle 25. In the position shown in FIG. 16, the device is pen-shaped. The cartridge 100 and roller assembly 4 reside in the front part of the handpiece.

Figure 17:
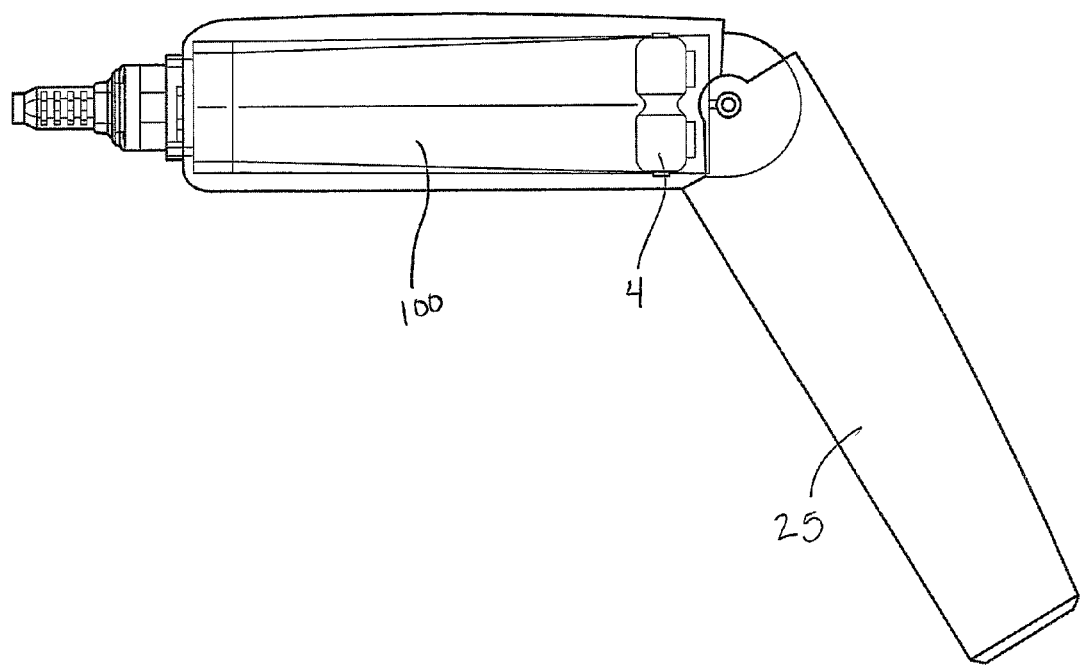
FIG. 17 demonstrates a gun-shaped handpiece with an articulated handle.

FIG. 17 shows the dispenser from FIG. 16 with the handle 25 in the gun-style position. The gun-style can be useful for filling trays whereas the pen-style can be useful for precision intra-oral work. This design permits the user to choose which configuration is most suitable.

The delivery device includes a display 33, such as an electronic digital display, that is visible to the user. The display 33 of the delivery device may display the battery level and amount of material remaining in the cartridge. In addition, the display 33 may also indicate the working time or mouth removal time (MRT). The delivery device may include several controls, such as a trigger 35 to depress for extruding material and at least one button for selecting programmed functions such as speed settings.

Figure 18:
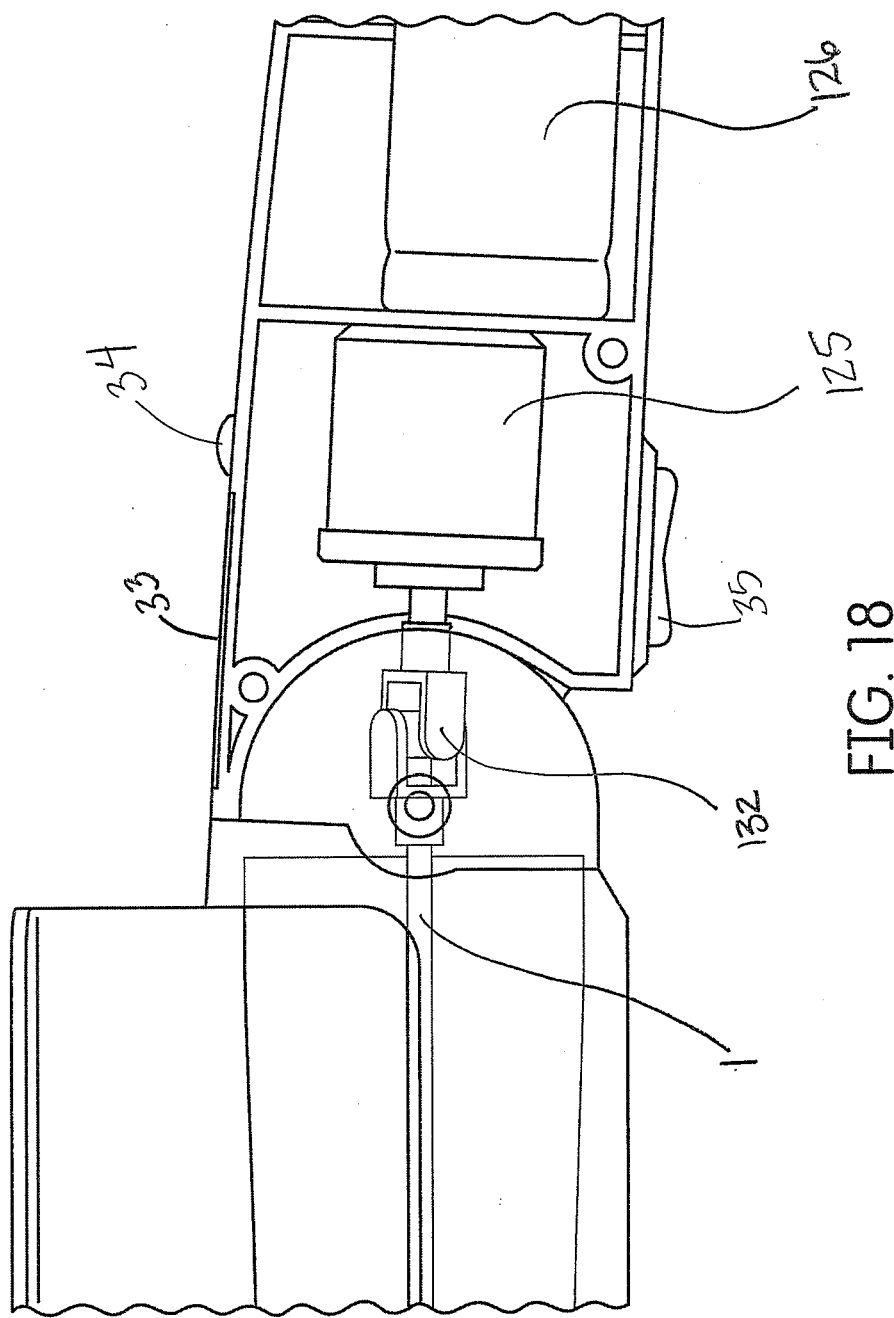
FIG. 18 illustrates the motor, battery and universal linkage located in the articulated handle of a handpiece.

FIG. 18 illustrates the motor 125, battery 126 and universal linkage 132 that are located in the articulated handle 25. The universal linkage 132 permits the motor to turn the drive shaft 1 regardless of the handle orientation. The control button 34, dispensing trigger 35 and display 33 can also be seen in FIG. 18.

Figure 19:
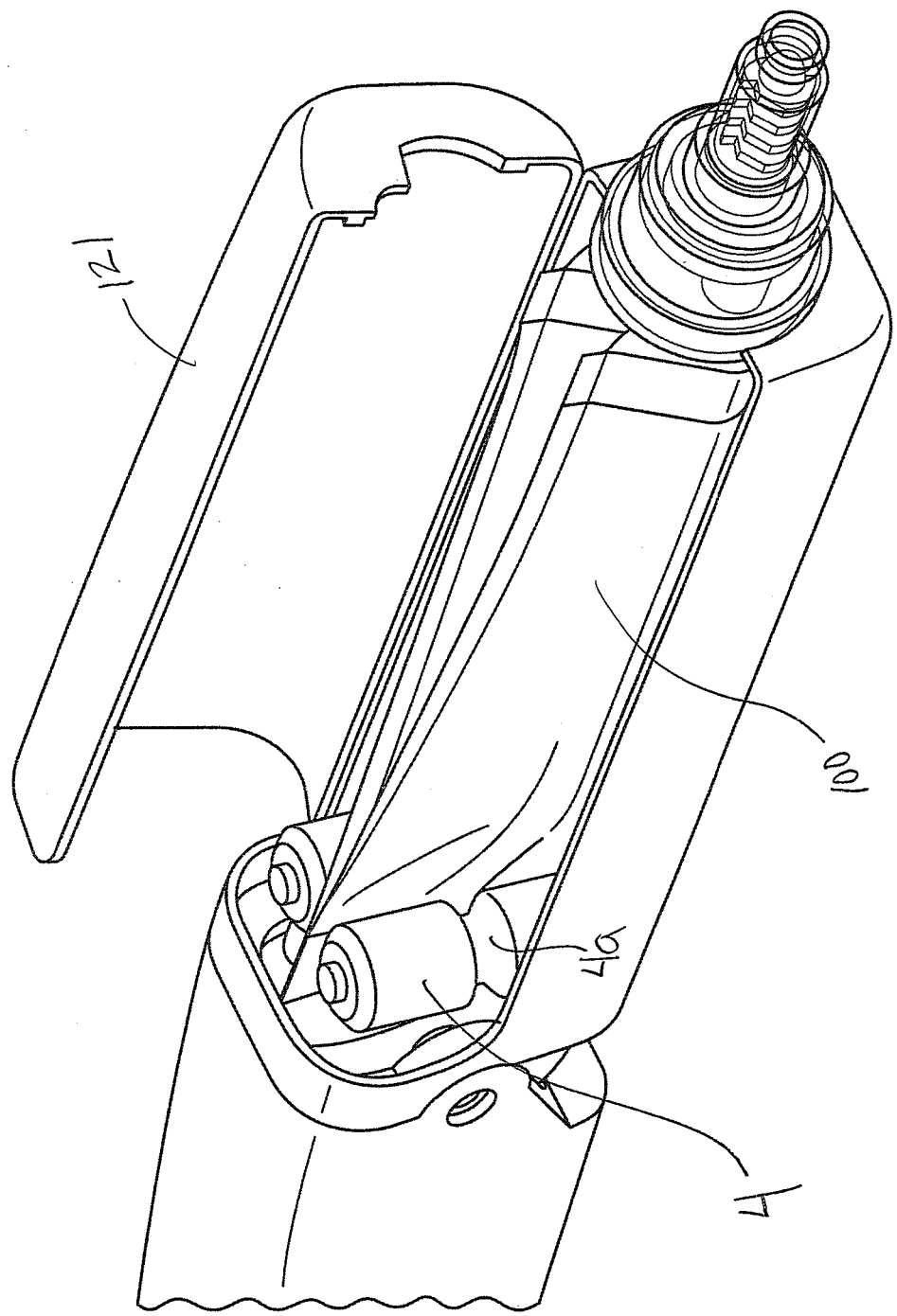
FIG. 19 shows the device of FIG. 16 with the hinged access door open.

FIG. 19 shows the device of FIG. 16 with the hinged access door 121 open. The track mechanism for the rollers 4 is not shown.

In yet further embodiments, the delivery device may include an illuminating light 36 that would provide illumination to the oral cavity. The LED would be mounted on the front of the handpiece and would be used during wash procedures. The light might have an on/off switch because it would not be necessary for tray procedures. Another optional feature may be external computer programming and communication. A user could receive software updates or diagnostic evaluations online via this connection. Yet another optional feature may be a capability to record specific details about the delivery device, such as how it was used and what materials were used (for example, how much material is used each time and for which products, how frequently certain products are used, and the like).

Another optional feature may be that the delivery device would be capable of reading a RFID label on the cartridge. The delivery device could identify the material and adjust dispensing rates accordingly (for example, fast for tray and slow for wash). The delivery device could then communicate material specific information such as MRT.

In yet alternative embodiments, a miniature camera could be mounted on the front of the delivery device and connected to a USB terminal. The camera could provide magnification on a nearby computer monitor to enhance the operator's precision.

One characteristic of the delivery device disclosed herein is the flexible film cartridge and the way in which it is assembled from individual pouches that are joined together to form a double cartridge. A unique spout fitment with a D-shaped flange facilitates this construction. Asymmetrical snap features on the spout fitment allow it to be joined to an identical fitment turned 180°.

Another unique feature is the use of a dynamic mixtip on a hand held device. Previously, dynamic mixtips were only used on table top, bulk dispensers. This dispenser incorporates the desirable benefits of a dynamic mixtip with the convenience of a handheld portable device.

The impression material dispensing system disclosed herein may utilize both dynamic 20 and static 29 (motionless) mixers. The dynamic mixtips 20 may be used for heavy body tray materials to reduce waste and increase dispensing rates. Static mixtips 29 may be used for light body wash materials because they are longer than dynamic mixtips 20 and the extra length is beneficial for intra-oral applications. The exit ports that connect to the spout 5 of connector portion 9 on wash materials may be configured differently than on tray materials to ensure that that the correct mixtip is always used.

Conventionally, the majority of impression materials are packaged in 50 mL rigid cartridges like the mixtips manufactured by Sulzer Mixpac. The cartridge or pouch system 100 disclosed herein is about 60 to 70% less packaging by weight because it is made from thin film laminates. In addition, the conventional, rigid cartridges are hollow and take up a lot of space in storage and transportation. The film laminate can be stored on a roll which takes up much less space. Therefore, the cartridge 100 disclosed herein reduces transportation packaging, handling, transportation and storage costs.

One dynamic mixtip 20 suitable for use and described herein results in 50% less product waste than the conventional static mixtip 29 used with conventional 50 mL rigid cartridges.

Ergonomics is improved with the powered delivery system described herein because all the operator needs to do is pull the trigger 35 to dispense the dental material, such as impression material. The current manual guns require the user to squeeze a handle which requires strength, stamina and tremendous effort to minimize tip movement, especially when dispensing wash material directly around a tooth preparatory area.

The conventional manual dispensers also position the user a large distance from the application site making it harder to control placement. The dispensing device disclosed herein positions the users hand much closer to the patient and application site making it much more ergonomic configuration.

Conventional dynamic mixtips are driven by a central shaft on the dynamic mixer, which couples to the mixtip by a recessed hex-shaped hole in the dynamic mixing element. The handpiece described herein has the drive shaft positioned off to the side so that it does not interfere with cartridge loading. The drive shaft runs forward so that the gearing engages with a gear mechanism on the mixtip described herein.

One known packaging format employed by 3M is generally referred to as sausage packs. These cylindrical, flexible pouches are crimped with metal ties at each end and resemble a package commonly used for packaging ground meat. These packs are used on 380 mL bulk dynamic mixers. The packs are placed into reusable cartridge bodies which contain the pouches as they are compressed for dispensing. The cartridge bodies also pierce the front of the pouches and facilitate connection to the dynamic mixtips. These intermediate cartridge bodies get messy and need to be cleaned. It's also cumbersome to unload the spent pouches. In contrast, embodiments of the system described herein do not require an intermediate container and have an integral rigid fitment on the front of the flexible cartridge assembly that directly connects to the dynamic mixtip, which is much easier and cleaner to use.

In embodiments described herein, it is described to have a flexible film cartridge without a drive shaft and a drive shaft in the handpiece and gearing mechanisms to engage a geared dynamic mixtip at the delivery end of the device.

In another embodiment, described is a drive shaft that is part of the flexible film cartridge. The drive shaft will extend between the spout packs and engage with a more traditional dynamic mixtip connection at the delivery end and a motor/transmission at the operator end of the device to provide rotational movement.

Yet another embodiment disclosed herein utilizes a tube-within-a-tube construction.

Another embodiment is a single pouch with a central divider. Such a pouch could be constructed from three layers of material, one on top of the other, with the central layer being the divider.

One embodiment of the roller rack assembly includes a screw and nut mechanism for advancing the rollers. Another embodiment has a rack and pinion, or worm gear mechanism.

Another embodiment of the cap or closure is a foil seal, induction heat sealed to the end of each outlet port.

Another embodiment includes motor torque sensing to adjust the delivery rate and to prevent over pressurizing of the flexible film cartridges.

Another embodiment disclosed herein includes controlling the position of the rollers by counting the number of rotations.

Another embodiment includes an auto back-off position wherein the rollers back up a slight amount after the trigger is released to eliminate unintentional oozing of the material in the cartridge, but not so far as to suck back air into the pouch.

Another embodiment has the rollers returning to the zero position (ready to load/full cartridge position) prior to opening and to do it more rapidly than when material is dispensed. When a partially used cartridge is placed in the handpiece and the door is closed, the rollers will advance to a point where pressure is sensed and then will back off to prevent inadvertent pressurization when changing tips.

Another embodiment includes a lock out latch on the door where the door cannot be opened unless the rollers are in the zero or original, rear position.

Another embodiment includes the use of a manual dispensing gun instead a powered dispenser.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. A cartridge, comprising:
a first pouch and a second pouch,
the first pouch having a first connector piece therein such that a fin portion of the first connector piece is inside and attached to the first pouch,
the second pouch having a second connector piece therein such that a fin portion of the second connector piece is inside and attached to the first pouch,
the first connector piece has a D-shaped connector portion that is connected to a D-shaped connector portion of the second connector piece via interlocking members to for a single connector thereby connecting the first pouch to the second pouch,
wherein each D-shaped connector portion has one spout such that the cartridge is capable of expelling one material from the first pouch and a second material from the second pouch, and
wherein the connector and the first pouch and the second pouch each have a groove therein to allow for a central drive shaft to pass through the cartridge.

2. The cartridge according to claim 1, wherein the first pouch and the second pouch have an inner heat seal layer such that the first pouch and second pouch can be adhered to each other.

3. The cartridge according to claim 1, wherein the first pouch and the second pouch are monolithic film substrate or a multi-layer film laminate.

4. The cartridge according to claim 1, wherein the first pouch includes a first dental material and the second pouch includes a second dental material.

5. A dispenser, comprising:
an outer housing having a trigger and a door suitable to access at least two roller rack assemblies inside of the housing,
each of the at least two roller rack assemblies include a roller having a pinion on each side such that each pinion is located between a pinion gear track and a worm gear, and
upon activation from the trigger, the roller advances along a length of the pinion gear track and worm gear, and
wherein the roller has a groove to accommodate a central drive shaft.

6. The dispenser according to claim 5, wherein the worm gears are rotated simultaneously with a central drive shaft.

7. A dispensing system comprising a cartridge and dispenser,
where the cartridge comprises a first pouch and a second pouch, the first pouch having a first connector piece therein such that a fin portion of the first connector piece is inside and attached to the first pouch, the second pouch having a second connector piece therein such that a fin portion of the second connector piece is inside and attached to the first pouch, the first connector piece has a D-shaped connector portion that is connected to a D-shaped connector portion of the second connector piece via interlocking members to for a single connector thereby connecting the first pouch to the second pouch, wherein each D-shaped connector portion has one spout such that the cartridge is capable of expelling one material from the first pouch and a second material from the second pouch, and
where the dispenser comprises an outer housing having a trigger and a door suitable to access at least two roller rack assemblies inside of the housing, each of the at least two roller rack assemblies include a roller having a pinion on each side such that each pinion is located between a pinion gear track and a worm gear, and upon activation from the trigger, the roller advances along a length of the pinion gear track and worm gear, and wherein the roller has a groove to accommodate a central drive shaft.

* * * * *